United States Patent [19]
Becker et al.

[11] Patent Number: 4,950,658
[45] Date of Patent: Aug. 21, 1990

[54] METHOD OF MEDICAL TREATMENT OF ALZHEIMER'S DISEASE

[75] Inventors: Robert E. Becker; Ezio Giacobini, both of Springfield, Ill.

[73] Assignee: Board of Trustees of Southern Illinois Univ., Springfield, Ill.

[21] Appl. No.: 280,570

[22] Filed: Dec. 6, 1988

[51] Int. Cl.$^5$ .............................................. A61K 31/66
[52] U.S. Cl. ..................................................... 514/129
[58] Field of Search .......................................... 514/129

[56] References Cited

U.S. PATENT DOCUMENTS

| | | | |
|---|---|---|---|
| 2,701,225 | 2/1955 | Lorenz | 167/22 |
| 3,067,096 | 12/1962 | Trace et al. | 167/53 |
| 3,111,457 | 11/1963 | Trace et al. | 167/53 |
| 3,233,513 | 12/1965 | Geary | 71/2.3 |
| 3,264,175 | 8/1966 | Heim | 167/22 |
| 3,801,710 | 4/1974 | Parish et al. | 424/222 |
| 4,141,975 | 2/1979 | Gay et al. | 424/217 |
| 4,277,467 | 7/1981 | Dorn et al. | 424/217 |
| 4,288,451 | 9/1981 | Mues et al. | 424/295 |

OTHER PUBLICATIONS

American Society of Hospital Pharmacists "American Hospital Formulary Service" p. 1376.
Copy of Computer Search Conducted in Dialog 2, Files 23,24,25,26,229,300,301,328,320,330,331,399,308,309,320,310 and 311.

*Primary Examiner*—Stanley J. Friedman
*Attorney, Agent, or Firm*—Anthony S. Zummer

[57] ABSTRACT

This invention relates to a method for improving memory and accompanying symptoms in patients with Alzheimer's disease and related disorders of memory. The method includes the steps of dosing a patient with 2,2-dichlorovinyl dimethyl phosphate sometimes referred to as dichlorvos or DDVP, or a precursor thereof maintaining said dosage at a level and over a period of time sufficient to create a concentration of DDVP in the brain whereby memory improvement occurs. A satisfactory precursor for this method is 2,2,2-trichloro-1-hydroxyethyl dimethyl phosphate sometimes referred to as metrifonate and 1,2-dibromo, 2-dichlorvoethyl dimethyl phosphate sometimes referred to as naled. Other precursors are also useful.

6 Claims, No Drawings

METHOD OF MEDICAL TREATMENT OF ALZHEIMER'S DISEASE

BACKGROUND OF THE INVENTION

1. Field of the Invention

This invention relates to a method for treating patients with Alzheimer's disease to improve memory impairment and accompanying symptoms commonly associated with Alzheimer's disease and related disorders of memory.

2. Description of the Prior Art

One important strategy in Alzheimer's disease has been to attempt to compensate for the disturbance in cholinergic function by increasing brain acetylcholine levels. This has been achieved using physostigmine and tetrahydroaminoacridine which induce acetylcholinesterase inhibition. Use of physostigmine and tetrahydroaminoacridine has important deleterious limitations in that (1) physostigmine is a very short acting inhibitor; (2) tetrahydroaminoacridine may be hepatotoxic; (3) the clinical effect of physostigmine and tetrahydroaminoacridine are variable; (4) the biochemical effects of these drugs on the level of inhibition of brain acetylcholinesterase and on acetylcholine concentration at synapse are not known; (5) the relationship between these clinical and biochemical effects is not known; (6) adequate levels of inhibition in brain may not have been achieved in clinical trials to date; and (7) assaying cholinergic markers is methodologically difficult.

Many of the methodological problems mentioned here are inherent in the use of short acting inhibitors such as physostigmine which do not provide a sufficiently long period of steady state inhibition to allow the various factors to come to equilibrium.

OBJECTS OF INVENTION

A principal object of the present invention is to provide a method for improving memory and accompanying symptoms in patients with Alzheimer's disease and related disorders of memory. The method includes the steps of dosing a patient with 2,2 dichlorovinyl dimethyl phosphate sometimes referred to as dichlorvos or DDVP or a precursor thereof, maintaining said dosage at a level and over a period of time sufficient to create a concentration of DDVP in the brain whereby memory improvement occurs.

Another principal object of the invention is to provide such a method for improving memory and accompanying symptoms in patients with Alzheimer's disease and related disorders of memory by dosing the patent with the precursors 2, 2, 2-trichloro-1-hydroxyethyl dimethyl phosphate sometimes referred to as metrifonate and 1, 2-dibromo-2, 2-dichlorvoethyl dimethyl phosphate sometimes referred to as naled. Other precursors are also useful.

SUMMARY OF THE INVENTION

The method of this invention for improving memory and accompanying symptoms in patents with Alzheimer's disease and related disorders of memory includes the steps of dosing the patient with 2, 2 dichlorovinyl dimethyl phosphate sometimes referred to as dichlorvos or DDVP or a precursor thereof, maintaining said dosage at a level and over a period of time sufficient to create a concentration of DDVP in the brain whereby memory improvement occurs.

A satisfactory precursor for this method is 2, 2, 2-trichloro-1-hydroxyethyl dimethyl phosphate sometimes referred to as metrifonate and 1, 2-dibromo-2, 2-dichlorvoethyl dimethyl phosphate sometimes referred to as naled. Other precursors may also be useful.

DESCRIPTION OF THE PREFERRED EMBODIMENT

We have discovered that 2, 2 dichlorovinyl dimethyl phosphate is suitable for palliative therapy of memory impairments and accompanying symptoms in patients with Alzheimer's disease and related disorders of memory. The concentration of 2, 2 dichlorovinyl dimethyl phosphate apparently compensates for the disturbance in cholinergic function by increasing brain acetylcholine levels. The 2, 2 dichlorovinyl dimethyl phosphate may be provided for the purpose by direct application or it may be provided by the application of precursors which transform to the active metabolic 2, 2 dichlorovinyl dimethyl phosphate, hereafter DDVP. Known precursors useful for this purpose are 2, 2, 2-trichloro-1-hydroxyethyl phosphate, hereafter referred to as metrifonate and 1, 2-dibromo-2, 2-dichlorvoethyl dimethyl phosphate hereafter referred to as naled. Other precursors may also be suitable for this purpose as will be readily available from description of this invention.

The treatment of Alzheimer's disease victims with DDVP, metrifonate or naled are safe and have few side effects. Any such side effects that do occur can easily be controlled by treatment with anticholinergics such as atropine, as will more fully be discussed later.

The use of DDVP metrifonate or naled as an insecticide for the treatment of schistosoma and other related diseases is well known. Examples of disclosures of such treatments are Holmstedt. B., Nordgren, I., Sandoz, M., and Sundwall, A., Arch. Toxicol. 41:329, 1978; Nordgren, I., Bergstrom, M., Holmstedt, B. and Sandoz, M., Arch. Toxicol. 41:3141, 1978; Nordgren, I., Holmstedt, B., Bengtsson, E. and Finkel, Y., Amer. J. Trop. Med. Hyg., 29(3):426430, 1980 and Nordgren, I. Quantitation of metrifonate and dichlorvos in blood and tissues by gas chromatography - mass spectrometry. Fund. Appl. Toxicol. 1:230–234, 1981. However, none of these operators realized the memory improvement obtainable by the use of these drugs. Our invention resides in the discovery that such products do result in memory improvement with patients with Alzheimer's disease and related disorders.

Cholinergic neurons in the basal forebrain undergo a profound (70–80%) selective damage and death in Alzheimer patients. Acetylcholine synthesis, choline acetyltransferase activity, acetylcholinesterase activity and choline uptake are all markedly reduced. The cholinergic neurons appear to play a fundamental role in cognitive functions, especially memory. These functions are selectively and irreversibly affected by Alzheimer's disease. In addition, transient memory enhancements with the acetylcholinesterase inhibitor physostigmine, orally or i.v. and tetrahydroaminoacridine have been demonstrated in Alzheimer patients. Since the reduction in choline acetyltransferase activity in the cortex correlates with the degree of cognitive impairment as well as with the severity of the neuropathological terminal changes of Alzehimer's disease a direct relationship between loss of forebrain cholinergic innervation and some symptoms of Alzheimer's disease seems likely. Based on the assumption that brain function in some Alzheimer's disease patients can be improved by increasing acetylcholine levels at the synapse physostigmine has been used to improve memory function. Interestingly, 6 out of 9 studies with i.v. administration of physostigmine and some studies of oral tetrahydroaminoacridine have shown improvement in memory.

DDVP is a potent (up to 96% inhibition) and rapidly active (within one minute) inhibitor of brain cholinesterase (Stavinoha, W. B., Modak, A. T. and Weintraub, S. T. J Neurochem 18:1375-1378, 1976). It leads to peak accumulation of acetylcholine within 5 minutes in the cortex, striatum, hippocampus and midbrain (Stavinoha et al, 1976). Thus the rate of accumulation appears to be more pronounced in three of the four regions that contain cholinergic nuclei or terminals (Modak, A. T., Stavinoha, W. B. and Weintraub, S. T., Arch. Int. Pharmacodyn. 27:293-301, 1975).

Two of these regions, the cortex and hippocampus, are sites of cholinergic damage in memory disorders. After acute administration of DDVP, to rats, normal acetylcholine levels are regained within 24 hours in all brain regions even though cholinesterase is still 35% inhibited (Modak et al, 1975). The dynamics of acetylcholine levels are not known under conditions of chronic administration of DDVP, particularly in humans with a cholinergic deficit.

Metrifonate is a drug which transforms to the active metabolite DDVP, the structural formulation for which is as follows:

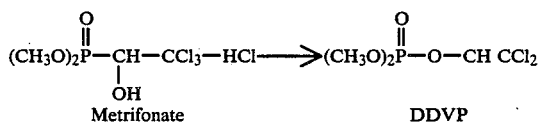

It has been widely used for treatment of schistosomiasis since 1960 (Lebrun, A. and Cerf, C. Bull. Med. Hlth Org. 22:579-582, 1960). It inhibits plasma acetycholinesterase for 5 days or longer following a single oral dose (7.5 mg/kg) (Nordgren et al., 1980). Intraperitoneal administration of metrifonate (125 mg/kg) in the mouse results in a 70% inhibition of brain acetylcholinesterase within 15 minutes and a simultaneous increase in acetylcholine, (Nordgren et al. 1978). Metrifonate is a precursor that is itself not active against acetylcholinesterase. DDVP is the active metabolite of metrifonate.

The success of the dosage schedule; 7.5-10 mg/kg body weight every 1-4 weeks, used in the chemotherapeutic treatment of schistosomiasis (Jewsburg, J. M., Cooke, M. J. and Weber, M. C. Ann. Trop. Med. Parasitol. 71:67-83, 1977) and 7.5 to 15 mg/kg body weight every two weeks; used for onchocerciasis (Salazar-Mallen, M. Ann. Trop. Med. Parasit. 65:393, 1971) is due to metrifonate acting as a slow release precursor for the anticholinesterase drug DDVP. A clinical slow release formulation of DDVP is also effective against parasite (Cervoni, W. A., Oliver-Gonzalex, J., Kay, S. and Slomka, M. D. Amer. J. Trop. Med. Hyg. 18:912-919, 1969) which is consistent with the inference that the DDVP formed from metrifonate is the active cholinergic agent (Nordgren et al, 1978).

Metrifonate is rapidly absorbed in humans and tolerated with relatively few side effects (Nordgren et al., 1978, 1980, 1981). The most common symptoms are those due to increased cholinesterase activity such as nausea, vomiting, transient vertigo and colic (Nordgren et al., 1978, 1980); (Nordgren, I., Bengtsson, E., Holmsted, B. and Pettersson, B.-M., Acta Pharmacol. et toxicol. 49 suppl V. 79-86, 1981). When these symptoms become clinically distressing they can be controlled by the administration of an anticholinergic drug. Since peripherally-active cholinergic antagonists are available, symptomatic control of side effects can be achieved without interference with the effects of this drug. Atropine has been most widely used to suppress side effects in antihelminthic therapy (Nordgren et al, 1981). We have not found it necessary to treat side effects in the 15 patients we have treated to date.

In the most recently published review of the world literature on metrifonate Nordgren et al (1981) concluded that the primary side effects were cholinergic i.e. nausea, colic, sweating, vomiting and lassitude. These side effects were held to be of mild degree in that they did not result in patients modifying their daily living activities (Nordgren et al, 1981). These side effects did not require anti-cholinergics, but could be easily relieved by anticholinergics. The safety of metrifonate is illustrated by the report (Svetlicic, B. and Wiihelm, K. Arch. Hyg. Rada, 19:241, 1968) that confirms other reports in the literature that even the symptoms of metrifonate overdose that result from self administration of large quantities of the drug can also be relieved by atropine (Holmsted 1978). In a 1974 review of the world literature and of field reports, the World Health Organization concurred that: "Cholinergic symptoms such as nausea, vomiting, bronchospasm, abdominal discomfort, diarrhea, and a feeling of weakness are rare at recommended dosage levels but were encountered in early trials, when doses now considered to be excessive were given. Atropine can be used for symptomatic relief and oximes are available for enzyme reactivation. Symptoms occurring at recommended dose levels usually disappear spontaneously in 12 to 24 hours" (WHO Expert Committee on Filariasis, Third Report Wld. Hlth. Org. Techn. Rep. Ser.. No. 542, 1974).

Metrifonate has distinct advantages that no other cholinesterase inhibitor is known to possess: it has low toxicity, requires only infrequent administration, is well absorbed after oral administration, and it achieves physiologically effective levels of inhibition of acetylcholinesterase in the central nervous system. The lack of frequent side effects, the mild and not disabling severity of the side effects when they do occur and the ease with which they can be controlled by anticholinergics are proving to be distinct clinical advantages of this drug. If metrifonate is found to be clinically useful the lack of side effects would be an advantage. In the elderly noncompliance with drug thereapy is increased when side effects occur (Williamson, J. and Chapin, J. M. Age and Ageing 9:73-80, 1980). The weekly dosing schedule is an additional aid to compliance. Merifonate has a half life of cholinestcrase inhibition of 5-6 days (Nordgren et al, 1980) which has made it clinically effective with weekly or less frequent administration. Prolonged activity also provides a distinct advantage in managing confused elderly who may not be capable of self administration and need to have drugs administered by a caretaker. Metrifonate is both oxidatively metabolized to active products and non-enzymatically converted to DDVP at a pH dependent rate (Nordgren et al, 1978). The basic metabolism of metrifonate to DDVP probably will not be changed in elderly although possible alterations in the rate of oxidative metabolism and changes in drug distribution in the elderly are best kept in mind in the development of dosage schedules. DDVP is rapidly inactivated by oxidative metabolism with loss of enzymatic inhibitory activity (Holmsted et al, 1978). Slowing of this oxidative step may result in some prolongation of cholinesterase inhibition in elderly males, more than in females. However, this should not reduce the drug's efficacy or increase side effects if appropriate dosage and dosing interval adjustments are identified and used. The rapid absorption, rapid distribution to the brain compartment and rapid conversion of metrifonate to DDVP provides the research advantage that both acute and long term cholinesterase inhibition effects can be studied. In summary, metrifonate has many kinetic and safety properties that suggest it would be consumer accepted, safe for widespread chronic administration, practical and convenient for administration to a dependent pupulation and probably easy to supervise after appropriate dosing parameters are identified for the elderly. There do not appear to be any known kinetic or safety impediments to the the study of metrifonate efficacy in Alzheimer disease.

Unlike metrifonate, which acts as a slow release formulation, naled degrades rapidly in vivo to the metabolite DDVP. We found the plasma cholinesterase inhibition by naled was parallel to that by DDVP whereas a 10-fold increase in metrifonate was necessary to obtain the same amount of inhibition. The slightly lower values in inhibition observed for naled than that of DDVP can be attributed to its higher molecular weight. This data indicates that naled is a precusor of DDVP without inherent cholinesterase inhibition activity of its own. All the cholinesterase inhibition activity of naled is a result of the formation of DDVP.

We have studied metrifonate in vitro and in vivo in the rat and compared its effects to the effects of other inhibitors of brain cholinesterase, physostigmine and tetrahydrominoacridine (Hallack and Giacobini 1987, Hallak and Giacobini 1988, Soininen et al.) After intramuscular administration of metrifonate (80 mg/Kg) the activity of cholinesterase decreased to 26% at 30 min. recovered to 50% at 180 min. and returned to 74% at 360 min. Levels of acetylcholine increased by 45% at 45 min. then returned to normal by 120 min. When metrifonate (2.5 mg) was given intracerebroventricularly the activity of cholinesterase decreased in the injected side at 30 min. to 20% in hippocampus, 22% in the medulla, 50% in the cerebellum, 58% in the striatum and 72% in the cortex. Levels of acetylcholine increased maximally at 45 min. in the hippocampus and cortex to 160% of baseline and peaked in the striatum at 60 min. at 155% of baseline.

The behavioral and adverse effects of cholinesterase inhibitors are not due solely to the cholinesterase inhibition but must result from differences in the mechanisms of action among the various cholinesterase inhibitors (Becker, R. E. and Giacobini, E., Drug Development Research 12:163-195, 1988). Comparison of the effects of physostigmine, metrifonate and tetrahydroaminocridine in rats supports this position. (Hallack and Giacobini 1988). Among these inhibitors, major differences in biochemical effects on rat brain include extent and duration of cholinesterase inhibition, inhibition of acetylcholine release and increase in levels of acetylcholine. Side effects are also markedly different in time of appearance, duration and severity.

In rats administered with metrifonate (80 mg/Kg 1M) side effects were both less frequent and less severe than with the other two drugs in spite of metrifonate producing the highest levels of peak cholinesterase inhibition. Symptoms developed at 20-35 mins. after the injection if metrifonate. Fasciculations, tremor, facial clonus and increased defecation were most common, seizures did not occur with metrifonate and all animals survived at the dosage used. This dosage has previously been shown to produce levels of cholinsterase inhibition and acetylcholine concentration increases almost equal to those produced by the $LD_{50}$ dose of physostigmine, 650 mg/Kg and greater than those produced by tetrahydroaminoacridine (Becker and Giacobini 1988). Yet with only 300 mg/Kg i.m. of physostigmine and 15 mg/Kg tetrahydroaminoacridine a broader range of more severe side effects occurred in more animals, these included physostigmine treated animals; fasciculations (60%), tremor (30%), splay of hind limbs (25%), facial clonus (15%) and sedation (10%) and in tetrahydroaminoacridine treated animals increased salivation (60%), lacrimation (40%), pronounced splay (35%), fasciculations (25%), tremor (25%), facial and forelimb clonus (10%) and generalized seizures (4%) occurring every 5-10 minutes.

At the doses used the peak cholinesterase inhibition varied in magnitude and time for the three inhibitors. Inhibition was highest (85%) for metrifonate at 30 min., middle (65%) for physostigmine at 15 min. and lowest (40%) for tetrahydroaminoacridine at 60 minutes.

The effects of two consecutive administrations of physostigmine, metrifonate and tetrahydroaminoacridine on acetylcholine levels in rat brain were studied. Following the first administration, acetylcholine levels increased by 70% both for physostigmine and tetrahydroaminoacridine and 45% for metrifonate. The peak value of acetylcholine was reached at 15 min. for physostigmine, at 30 min. for tetrahydroaminoacridine and at 45 min. for metrifonate. Acetylcholine returned practically to control levels at 60, 90 and 300 min. following physostigmine, metrifonate and tetrahydroaminoacridine treatment, respectively.

The second administration of the drugs was timed so as to allow acetylcholine levels to return to approximately (+12%) control levels and the concentration of the drug was the highest that would allow 100% survival. Major differences in the pattern of acetylcholine accumulation were seen following this second consecutive administration of the inhibitor. The most striking finding was that brain acetylcholine level seen with the second administration of physostigmine was of the same order (75%) and duration (60 min.) as that seen after the first administration. With metrifonate, the maximal increase in acetylcholine after the second dosage was 33% as compared to a 45% increase after the first dose. Both of these effects were significant, however, they were not significantly different from each other. The increase in acetylcholine levels was more significantly prolonged following the second dosage of metrifonate as compared to the increase which followed the first treatment (120 min. vs. 90 min.). With a second administration of tetrahydroaminoacridine, there was no further increase in acetylcholine levels with respect to controls. On the contrary, at 120 min. after the second administration of tetrahydroaminoacridine, acetylcholine levels were 25% below control values (Hallak and Giacobini, 1988).

We have also studied $^3$H-choline accumulation and K+ evoked acetylcholine release at a concentration of metrifonate, physostigmine and tetrahydroaminoacridine that achieve 100% inhibition of cholinesterase activity in vitro. We found significantly less $^3$H choline accumulation only after the first does of tetrahydroaminoacridine and significantly more $^3$H acetylcholine release with physostigmine after each of two doses of drug. Synthesis of $^3$H acetylcholine was significantly lower in the presence of tetrahydroaminoacridine. (DeSarno and Giacobini 1988).

We have administered metrifonate to 15 Alzheimer's disease patients. Patients were diagnosed using Diagnostic Statistical Manual IIIR criteria. Probable Alzheimer's disease patients were then screened using strict inclusion and exclusion criteria to identify patients whose potential clinical response to cholinesterase inhibition would not be significantly affected by coexisting disease or concurrent administration of psychoactive drugs. Patients with moderately severe Alzheimer's disease were accepted to explore for effects of severity on drug response.

Patients were tested using the Alzheimer's Disease Assessment Scale (ADAS) (Rosen et al 1984), Mini Mental State Examination (Folstein et al 1975), a Clincial Global Assessment Scale (Guy 1973) and a rating scale for side effects. A laboratory battery to assess hematopoietic, hepatic, urinary and cardiac status, physical examination, vital signs and measurement of blood cholinesterase activities were completed. Patients were then given in a single oral dose under open conditions metrifonate 2.5 mg/Kg and 5 mg/Kg on successive weeks and reassessed 1, 4 and 7 days after the 2.5 mg/Kg dose and 4 and 7 days after the 5 mg/Kg dose. Patients were next administered metrifonate one month later after a second baseline assessment (blood cholinesterase have returned to initial values by 1 month) and were given on four successive weeks 7.5 mg/Kg, 7.5 mg/Kg, 15 mg/Kg and 15 mg/Kg and assessed 7 days after each dosing prior to administration of the next dose. At each assessment all the cognitive and medical studies at baseline were repeated.

To identify responders we used the criterion of an improvement of 4 points on the ADAS. Among 5 patients who have received all four dosage levels we have identified 5 as responders, among 10 patients who have received both the 2.5 and 5 mg/Kg doses we have identified 5 responders for a total of 10 responders identified. All of our "responders" had a change of 9 or more on the ADAS. The longest term patients (n=5) were on metrifonate for a total of four months.

In the completed patients the preferred dose, defined as maximum improvement without interfering side effects, was identified. Best doses ranged from 2.5 to 7.5 mg/Kg. Lower doses of about 0.5 mg/Kg were also operable. The highest dose of metrifonate (15 mg/KG) resulted in deterioration in cognitive performance which means there is a therapeutic window that roughly ranges from 2.5 to 7.5 mg metrifonate per Kg per week.

In sum we have successfully administered metrifonate to 15 patients (4-16 weeks of once weekly drug) without the appearance of side effects except for nausea and vomiting in four patients that has not reoccurred following administration of the highest dose as a divided dose over two days. We have achieved up to 80% inhibition of plastic cholinesterase and acetylcholinesterase in blood. We have identified patients who appear to respond to metrifonate with improved scores in the ADAS. We have found a suggestion in the preliminary work of a "therapeutic window" within which clinical response is maximal. This window with metrifonate preferably ranges from 30 to 60% inhibition of blood cholinesterase.

Thus, we have discovered that the once weekly dosing of the preferred drug of this invention metrifonate, a precursor for dichlorvos, at doses ranging from 0.5 to 15 mg/Kg body weight/week provides improvement in memory, cognition and other behaviors, in a significant number of Alzheimer's disease patients. Weekly administration of this dose has been used by us as a treatment for the symptoms of Alzheimer's disease. At these doses, up to 15 mg/Kg body weight/week, adverse, side or toxic effects have not occurred with the exception of occasional reports of nausea and vomiting on one occasion which has been handled by giving the drug in divided doses over two or more days.

What is claimed is:

1. The method of improving memory and accompanying symptoms in patients with Alzheimer's disease and related disorders of memory including the steps of
   (1) administering to a patient having Alzheimer's disease by dosage a suitable brain concentration of 2, 2 dichlorovinyl dimethyl phosphate and
   (2) maintaining said concentration at a level and over a sufficient period of time to provide said memory improvements.

2. The method of claim 1 wherein said brain concentration of 2, 2 dichlorovinyl dimethyl phosphate is provided by administering a drug chosen from the class consisting of 2, 2 dichlorovinyl dimethyl phosphate; 2, 2, 2-trichloro-1-hydroxyethyl dimethyl phosphate and 1, 2-dibromo-2, 2-dichloroethyl dimethyl phosphate.

3. The method of claim 1 wherein said brain concentration of 2, 2 dichlorovinyl dimethyl phosphate is provided by administering the precursor drug 2, 2, 2-trichloro-1-hydroxyethyl dimethyl phosphate.

4. The method of claim 3 wherein said 2, 2, 2-trichloro-1-hydroxyethyl dimethyl phosphate is administered in doses ranging from about 0.5 to 15 mg/Kg of body weight/week.

5. The method of claim 3 wherein said 2, 2, 2-trichloro-1-hydroxyethyl dimethyl phosphate is administered in doses ranging from about 2.5 to 7.5 mg/Kg of body weight/week.

6. The method of improving memory and accompanying symptoms of Alzheimer's disease and related disorders of memory including the steps of
   (1) administering to a patient having Alzheimer's disease a suitable dosage of 2,2,2-trichloro-1-hydroxyethyl dimethyl phosphate to create from 30-60% inhibition of blood cholinesterase and;
   (2) maintaining said inhibition level over a sufficient period of time to provide said memory improvements.

* * * * *